(12) United States Patent
White et al.

(10) Patent No.: US 8,901,077 B2
(45) Date of Patent: Dec. 2, 2014

(54) DELIVERY OF A GENE THERAPY VECTOR TO THE BRAIN BY CONVECTION-ENHANCED DELIVERY

(75) Inventors: Edward White, Bristol (GB); Steven Streatfield Gill, Bristol (GB)

(73) Assignee: Renishaw (Ireland) Limited, Wotton-under-Edge (GB)

(*) Notice: Subject to any disclaimer, the term of this patent is extended or adjusted under 35 U.S.C. 154(b) by 0 days.

(21) Appl. No.: 13/979,032

(22) PCT Filed: Jan. 23, 2012

(86) PCT No.: PCT/GB2012/000062
§ 371 (c)(1),
(2), (4) Date: Jul. 10, 2013

(87) PCT Pub. No.: WO2012/098367
PCT Pub. Date: Jul. 26, 2012

(65) Prior Publication Data
US 2013/0296246 A1 Nov. 7, 2013

(30) Foreign Application Priority Data

Jan. 22, 2011 (GB) .................................. 1101167.3

(51) Int. Cl.
| | | |
|---|---|---|
| A61K 48/00 | (2006.01) | |
| C07K 14/765 | (2006.01) | |
| C12N 15/86 | (2006.01) | |
| C12N 15/87 | (2006.01) | |

(52) U.S. Cl.
CPC ......... *A61K 48/0083* (2013.01); *A61K 48/0008* (2013.01); *A61K 48/0075* (2013.01); *C07K 14/765* (2013.01); *C12N 15/86* (2013.01); *C12N 15/87* (2013.01); *C12N 2710/16643* (2013.01)
USPC ...................................................... 514/15.2

(58) Field of Classification Search
None
See application file for complete search history.

(56) References Cited

PUBLICATIONS

Hadjipanayis et al (Mol Ther (Nov. 2008) 16(11): 1783-1788).*
Chen et al (J Neurosurg (2005) 103: 311-319).*
Sanders (J Neuro-oncol (Jul. 2002) 58(3): 187-192).*
Ries et al (DDT (Sep. 2004) 9(17): 759-768).*
Bobo et al., "Convection-enhanced delivery of macromolecules in the brain," *Proc. Natl. Acad. Sci.*, 1994, vol. 91, pp. 2076-2080.
Bowers et al., "Immune responses to replication-defective HSV-1 type vectors within the CNS: implications for gene therapy," *Gene Therapy*, 2003, vol. 10, pp. 941-945.
Canoll et al., "The interface between glial progenitors and gliomas," *Acta Neuropathol*, 2008, vol. 116, pp. 465-477.
Chen et al., "Surface properties, more than size, limiting convective distribution of virus-sized particles and viruses in the central nervous system," *J Neurosurg.*, 2005, vol. 103, pp. 311-319.
Dempsey et al., "Assessment of $^{123}$I-FIAU imaging of herpes simplex viral gene expression in the treatment of glioma," *Nuclear Medicine Communications*, 2006, vol. 27, pp. 611-617.
Fiandaca et al., "Real-time MR imaging of adeno-associated viral vector delivery to the primate brain," *NeuroImage*, 2008, pp. 1-9.
Harrow et al., "HSV1716 injection into the brain adjacent to tumour following surgical resection of high-grade glioma: safety data and long-term survival," *Gene Therapy*, 2004, vol. 11, pp. 1648-1658.
He et al., "The $\gamma_1 34.5$ protein of herpes simplex virus 1 complexes with protein phosphatase 1α to dephosphorylate the α subunit of the eukaryotic translation initiation factor 2 and preclude the shutoff of protein synthesis by double-stranded RNA-activated protein kinase," *Proc. Natl. Acad. Sci.*, 1997, vol. 94, pp. 843-848.
Hess et al., "Malignant glioma: patterns of failure following individually tailored limited volume irradiation," *Radiotherapy & Oncology*, 1994, vol. 30, pp. 146-149.
Jacobs et al., "HSV-1-Based Vectors of Gene Therapy of Neurological Diseases and Brain Tumors: Part II. Vector Systems and Applications," *Neoplasia*, 1999, vol. 1, No. 5, pp. 402-416.
Louis, David, "Molecular Pathology of Malignant Gliomas," *Annu. Rev. Pathol. Mech. Dis.*, 2006, vol. 1, pp. 97-117.
Mackay et al., "Distribution in brain of liposomes after convection enhanced delivery; modulation by particle charge, particle diameter, and presence of steric coating," *Brain Research*, 2005, vol. 1035, pp. 139-153.
Markert et al., "Conditionally replicating herpes simplex virus mutant, G207 for the treatment of malignant glioma: results of a phase I trial," *Gene Therapy*, 2000, vol. 7, pp. 867-874.
Marmarou et al., "Biomechanics of Brain Edema and Effects on Local Cerebral Blood Flow," *Advances in Neurology*, 1980, vol. 28, pp. 345-358.
Mastakov et al., "Recombinant Adeno-associated Virus Serotypes 2- and 5-Mediated Gene Transfer in the Mammalian Brain: Quantitative Analysis of Heparin Co-infusion," *Molecular Therapy*, 2002, vol. 5, No. 4, pp. 371-380.
McMahon et al., "CNS dendritic cells: Critical participants in CNS information?" *Neurochemistry International*, 2006, vol. 49, pp. 195-203.
Morrison et al., "High-flow microinfusion: tissue penetration and pharmacodynamics," *American Journal of Physiology—Regulatory, Integrative and Comparative Physiology*, 1994, pp. 292-305.

(Continued)

*Primary Examiner* — Karlheinz R Skowronek
*Assistant Examiner* — Mindy Newman
(74) *Attorney, Agent, or Firm* — Oliff PLC

(57) ABSTRACT

The invention relates to a composition comprising albumin and a therapeutic agent, particularly a gene therapy vector. The composition is useful in the treatment of glioma.

12 Claims, 10 Drawing Sheets

(56) References Cited

PUBLICATIONS

Figure 1:
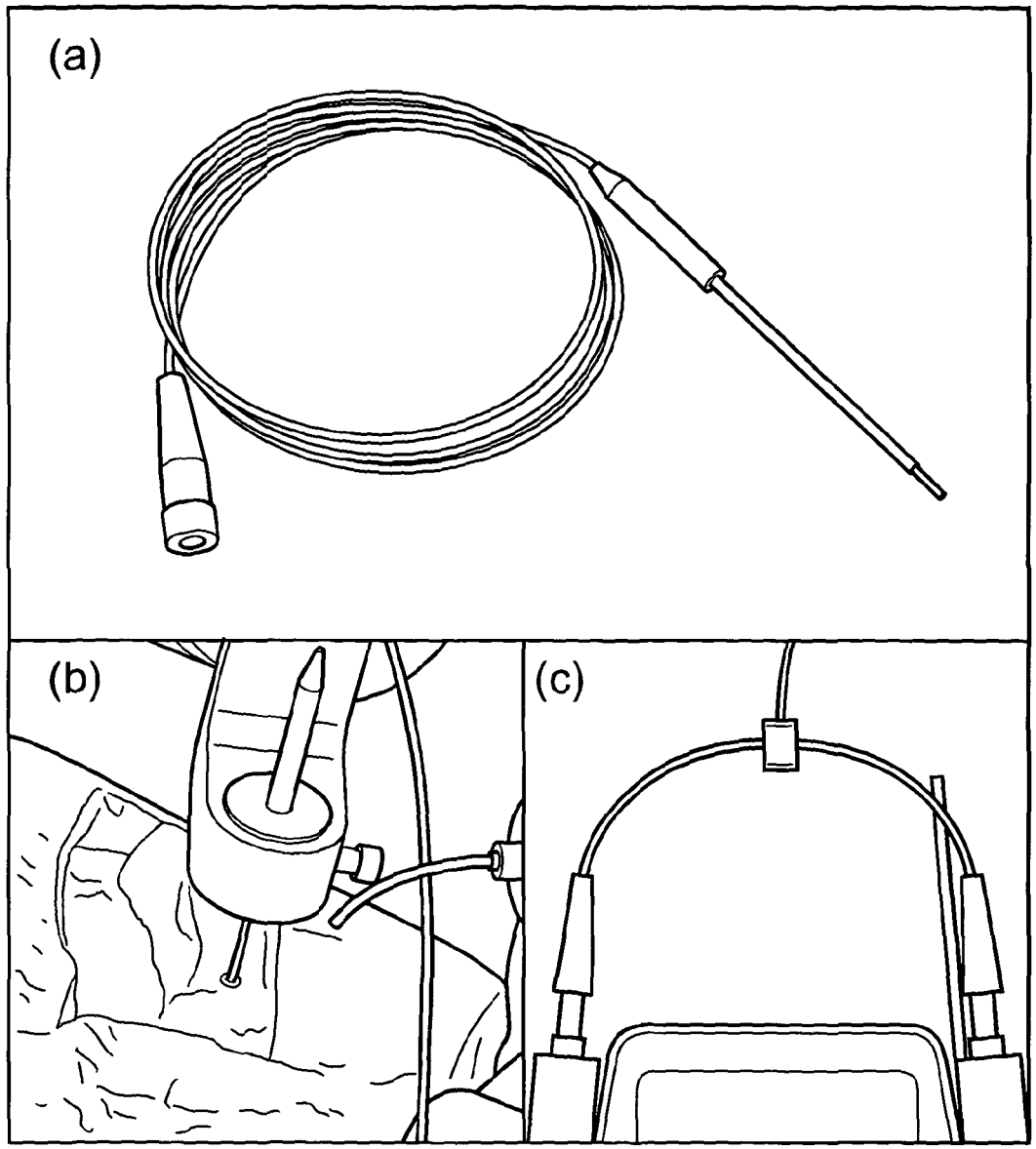

Neeves et al., "Dilation and degradation of the brain extracellular matrix enhances penetration of infused polymer nanoparticles," *Brain Research*, 2007, vol. 1180, pp. 121-132.

Nguyen et al., "Convection-enhanced delivery of AAV-2 combined with heparin increases TK gene transfer in the rat brain," *NeuroReport*, 2001, vol. 12, No. 9, pp. 1961-1964.

Papanastassiou et al., "The potential for efficacy of the modified (ICP 34.5) herpes simplex virus HSV1716 following intratumoural injection into human malignant glioma: a proof of principle study," *Gene Therapy*, 2002, vol. 9, pp. 398-406.

Rampling et al., "Toxicity evaluation of replication-competent herpes simplex virus (ICP 34.5 null mutant 1716) in patients with recurrent malignant glioma," *Gene Therapy*, 2000, vol. 7, No. 10, pp. 859-866.

Shah et al., "Oncolytic viruses: clinical applications as vectors for the treatment of malignant gliomas," *Journal of Neuro-Oncology*, 2003, vol. 65, pp. 203-226.

Shieh et al., "Cell Surface Receptors for Herpes Simplex Virus Are Heparan Sulfate Proteoglycans," *The Journal of Cell Biology*, 1992, vol. 116, No. 5, pp. 1273-1281.

Szerlip et al., "Real-time imaging of convection-enhanced delivery of viruses and virus-sized particles," *J. Neurosurg.*, 2007, vol. 107, pp. 560-567.

Thorne et al., "In vivo diffusion of lactoferrin in brain extracellular space is regulated by interactions with heparan sulfate," *PNAS*, 2008, vol. 105, No. 24, pp. 8416-8421.

Todo et al., "Systemic Antitumor Immunity in Experimental Brain Tumor Therapy Using a Multimutated, Replication-Competent Herpes Simplex Virus," *Human Gene. Therapy*, 1999, vol. 10, pp. 2741-2755.

Wrensch et al., "Epidemiology of primary brain tumors: Current concepts and review of the literature[1]," *Neuro-Oncology*, 2002, pp. 278-299.

Wudunn et al., "Initial Interaction of Herpes Simplex Virus with Cells Is Binding to Heparan Sulfate," *Journal of Virology*, 1989, vol. 63, No. 1, pp. 52-58.

Allard et al., "Convection-enhanced delivery of nanocarriers for the treatment of brain tumors," *Biomaterials*, 2009, vol. 30, pp. 2302-2318.

Hadjipanayis et al., "Therapeutic efficacy of a herpes simplex virus with radiation or temozolomide for intracranial glioblastoma after convection-enhanced delivery," *Mol Ther*, 2008, vol. 16, No. 11, pp. 1-17.

Huynh et al., "Barriers to carrier mediated drug and gene delivery to brain tumors," *Journal of Controlled Release*, 2006, vol. 110, pp. 236-259.

Ries et al., "Oncolytic viruses for the treatment of cancer: current strategies and clinical trials," *DDT*, 2004, vol. 9, No. 17, pp. 759-768.

White et al., "Evaluation and optimization of the administration of a selectively replicating herpes simplex viral vector to the brain by convection-enhanced delivery," *Cancer Gene Therapy*, 2011, vol. 18, pp. 358-369.

Chen, "Small-molecule delivery by nanoparticles for anticancer therapy," *Trends in Molecular Medicine*, 2010, vol. 16, No. 12, pp. 594-602.

Mar. 30, 2012 International Search Report issued in International Patent Application No. PCT/GB2012/000062.

Office Action dated Jun. 6, 2014 issued in Chinese Patent Application No. 201280006019.6 (with English translation).

\* cited by examiner

DELIVERY OF A GENE THERAPY VECTOR TO THE BRAIN BY CONVECTION-ENHANCED DELIVERY

FIELD OF THE INVENTION

The invention relates to the compositions and compounds for use in the treatment of gliomas.

BACKGROUND TO THE INVENTION

Malignant gliomas are the most common primary brain tumour and are associated with a very poor prognosis (Wrensch et al, 2002). It has been hypothesised that gliomas arise from endogeneous glial progenitor or neural stein cells (Canoll and Goldman, 2008), with which they share the ability to migrate along white matter tracts and perivascular and subpial spaces (Louis, 2006). As a consequence, malignant gliomas are highly infiltrative tumours for which complete surgical resection is not feasible. The limitations of conventional treatment modalities at adequately treating infiltrative tumour cells are highlighted by the observation that 80% of malignant gliomas recur within 2 to 3 cm of the original tumour mass (Hess et al, 1994).

Herpes Simplex Virus (HSV-1) is a large, naturally neurotropic, double-stranded DNA virus that is actively being developed into useful replication-selective (oncolytic) and replication-defective gene therapy vectors (Bowers et al, 2003). To date, two replication-selective viral constructs have reached clinical trials in patients with malignant gliomas (Rampling et al, 2000; Marken et al, 2000; Papanastassiou et al, 2002; Harrow et al, 2004). These viruses, designated G207 and HSV1716, harbour null mutations in both copies of the $\gamma_1 34.5$ gene. The products of this gene are critical in enhancing the ability of HSV-1 to infect neurones and overcome host cell responses to viral infection (He et al, 1997). In addition, null mutations of the $\gamma_1 34.5$ gene confer the ability of these vectors to selectively replicate in tumour cells (Shah et al, 2003).

To date, in all clinical trials of selectively-replicating HSV-1, vector administration has been achieved by direct intratumoural or intraparenchymal injection. Early clinical trials involved the direct injection of vector directly into the MRI-enhancing tumour mass (Rampling et al, 2000; Marken et al, 2000; Papanastassiou et al, 2002). These studies demonstrated safety and provided limited evidence of in vivo replication of HSV1716 in patients with malignant gliomas. However, conclusive evidence of significant vector distribution and treatment efficacy has yet to be demonstrated. Although this may relate to methodological difficulties of confirming vector replication clinically, there is significant uncertainty regarding the effectiveness of intratumoural injection (Dempsey et al, 2006).

By definition Grade IV gliomas are characterised by areas of tissue necrosis (World Health Organisation, 2007). Consequently the direct inoculation of a necrotic primary tumour mass with a replication-selective viral vector capable of replicating within live malignant glioma cells is unlikely to efficiently treat either the primary tumour mass or more importantly, the infiltrating tumour cells. In addition, the primary tumour mass is often amenable to surgical resection rendering intratumoural injection of replication-selective vector unnecessary. Indeed, Harrow et al (2004) undertook a phase I/II study of peri-tumoural injections of HSV1716 in patients undergoing resection of either recurrent or newly diagnosed malignant gliomas. This study demonstrated this approach to be safe, although it is clearly critical that for this approach to be efficacious, viral distribution must be optimised to facilitate the transduction of as many infiltrating tumour cells as possible.

Convection-enhanced delivery (CED) involves the use of fine catheters and precisely controlled infusion rates to distribute therapeutic agents by bulk-flow directly into the brain extracellular space, possibly along the same extracellular pathways that glioma cells are able to migrate. In contrast to techniques of drug delivery that depend on diffusion to achieve adequate drug distribution, such as carmustine-impregnated biodegradable polymers, with CED it is possible to distribute drugs homogeneously over potentially large volumes of brain, irrespective of the molecular size of the therapeutic agent (Morrison et al, 1994). As such it is an ideal technique for the administration of viral vector-mediated gene therapy to the brain of patients with malignant gliomas.

HSV-1 vectors have a diameter of 120 to 300 nm (Jacobs et al, 1999), whereas on average the brain extracellular space has a diameter of 38 to 64 nm (Thorne and Nicholson, 2006). Clearly this has the potential to make the administration of HSV-1-based vectors by CED unachievable. Consequently, in this study the distribution of a replication-selective HSV-1 viral construct by CED has been examined in both grey and white matter and, a variety of strategies to enhance viral vector distribution have been evaluated.

Nevertheless, in addition to the aforementioned clinical trials (6-9), HSV vectors have been administered by stereotactic injection into normal mouse (17-19), rat (20-26) and primate brains (20-28), animal models of high-grade glioma (29-35), mucopolysaccharidosis type VII(36), GM2 gangliosidosis (37) and Parkinson's disease (37-39), as well as being administered by CED into a glioma rat model (40). In view of this large number of studies it is surprising that to date no attempt has been made to systematically evaluate and optimise the delivery of these vectors directly into the brain. Consequently, in this study the distribution of a replication-selective HSV-1 viral construct by CED has been examined in both grey and white matter and, a variety of strategies to enhance viral vector distribution have been evaluated.

SUMMARY OF THE INVENTION

Based on the study, the inventors have identified compositions and compounds useful for optimising the delivery of therapeutic agents to white matter, especially by convection enhanced delivery. This is particularly useful for the delivery of gene therapy vectors.

A first aspect of the invention provides a pharmaceutical composition comprising a therapeutic agent and albumin or a functionally effective fragment thereof.

The composition preferably comprises a therapeutic agent for treatment of a neurological disease. The therapeutic agent is preferably for the treatment of a disease of the brain or spinal cord, especially a disease of the brain. It may be a cancer, especially a cancer of white matter, in particular a glioma. Alternatively, it may be any other appropriate neurological disease, especially a white matter disease such as multiple sclerosis.

The therapeutic agent may be any agent for treatment of a neurological disease, such as a gene therapy agent, especially a gene therapy vector. Alternatively, it may be pharmaceutical agent, such as a neurotrophic factor, especially glial cell derived neurotrophic factor (GDNF); an antibody or fragment thereof; an immunosuppressant; an immunomodulator, especially fingolimod; a cytokine, especially an interferon, such as interferon 1 alpha or beta; or an anti-inflammatory.

A gene therapy vector is any vector that may be used to introduce genetic Material into a cell. Gene therapy, as is well known, is the use of genetic material to modulate or add to genes in an individual's cells in order to treat disease. The genetic material to be introduced may be any appropriate genetic material, including DNA and RNA. The genetic material may be used to treat the disease in any known manner, such as gene replacement, gene knockdown, pro-survival gene therapy and cell suicide therapy.

The gene therapy vector may be any vector suitable for administering a gene therapy to a subject, including, for example, viral vectors. Any appropriate viral vector may be used, such as a herpes simplex virus vector, especially HSV-1; an adenovirus vector or a lentivirus vector. It is preferred that the viral vector is a large vector, at least 100 nm in diameter. Further it is preferred that it binds to the heparin binding receptor.

The composition additionally comprises albumin or a functional fragment thereof. As mentioned, the composition may be used for gene therapy. Albumin is included in the composition firstly to open up spaces between cells to enable the therapeutic agents, especially large viral vectors, to move more easily between cells. It also blocks heparin receptors on cells, which are low specificity binding receptors which bind to a variety of proteins, including heparin, albumin and to HSV vectors. By blocking the heparin receptors with albumin, binding of HSV to the receptors is reduced, increasing the proportion of HSV available for transduction. The albumin may be replaced with another heparin receptor binding agent, such as heparin itself, but albumin is preferred. A functional fragment of albumin is a fragment which binds to heparin receptors with at least 75% of the binding efficacy as the full length protein.

The composition preferably further comprises cerebrospinal fluid (CSF), especially artificial cerebrospinal fluid. Artificial cerebrospinal fluid is well known in the art and is a fluid which mimics natural CSF, particularly in terms of its salt contents. Preferably the composition comprises NaCl at a similar concentration to that found in natural CSF, that is to say the concentration is preferably within 15%, more preferably within 10% of the concentration in natural CSF. Preferably the composition comprises $NaHCO_3$ at a similar concentration to that found in natural CSF, that is to say the concentration is preferably within 15%, more preferably within 10% of the concentration in natural CSF. Preferably the composition comprises KCl at a similar concentration to that found in natural CSF, that is to say the concentration is preferably within 15%, more preferably within 10% of the concentration in natural CSF. Preferably the composition comprises $NaH_2PO_4$ at a similar concentration to that found in natural CSF, that is to say the concentration is preferably within 15%, more preferably within 10% of the concentration in natural CSF. Preferably the composition comprises $MgCl_2$ at a similar concentration to that found in natural CSF, that is to say the concentration is preferably within 15%, more preferably within 10% of the concentration in natural CSF. Preferably the composition comprises glucose at a similar concentration to that found in natural CSF, that is to say the concentration is preferably within 15%, more preferably within 10% of the concentration in natural CSF. Alternatively, the artificial CSF may omit glucose, so as to reduce the likelihood of bacterial growth in any catheter used to administer the composition to a subject.

The composition may further comprise other active agents. Pharmaceutical compositions of this invention may also comprise any pharmaceutically acceptable carrier, adjuvant or vehicle. Pharmaceutically acceptable carriers, adjuvants and vehicles that may be used in the pharmaceutical compositions include, but are not limited to, ion exchangers, alumina, aluminium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered by any appropriate route, but are preferably administered via injection, especially via a neurocatheter, in particular by convection enhanced delivery. The pharmaceutical compositions may contain any conventional non-toxic pharmaceutically-acceptable carriers, adjuvants or vehicles.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The composition may further comprise a label, enabling the composition to be identified or visualised particularly after administration. Any appropriate label may be used, such as a radioactive label. Such labels are known in the art.

A second aspect of the invention provides the composition of the first aspect for use in therapy.

A third aspect of the invention provides the composition of the first aspect for use in the treatment of a neurological disease.

A fourth aspect of the invention provides a method for treating a neurological disease comprising administering a composition according to the invention to a subject in need thereof.

A fifth aspect of the invention provides a method for improving the transduction of gene therapy vectors, especially into white matter cells, comprising administering albumin or a functional fragment thereof to a subject. The aspect may alternatively provide a method for reducing the therapeutically effective dose of a gene therapy vector, comprising administering albumin or a functional fragment thereof to a subject that is to receive the gene therapy vector. Therapeutically effective dose means the dose required to achieve a particular therapeutic effect, such as transduction of a certain area or number of cells. Reducing the therapeutically effective dose means that a smaller dose may be administered than is required without the administration of albumin.

A sixth aspect of the invention provides a method for improving the infusion of therapeutic agents through white matter, comprising administering albumin or a functional fragment thereof to a subject.

A seventh aspect of the invention provides albumin or a functional fragment thereof for use in the treatment of a neurological disease, especially a disease of the white matter. The albumin may also be for improving the transduction of a gene vector into cells or tissue, especially into white matter, glial or glioma cells.

An eighth aspect of the invention provides a therapeutic agent for use in the treatment of neurological disorder, wherein the therapeutic agent for administration to a subject to which albumin or a functional fragment thereof has been administered or is for simultaneous administration with albumin or a functional fragment thereof.

In the second to eighth aspects, the neurological disease is preferably a disease of the brain or spinal cord, especially a disease of the brain. It may be a cancer, especially a cancer of white matter, in particular a glioma. Alternatively, it may be any other appropriate neurological disease, especially a white matter disease such as multiple sclerosis.

In particular, in the fifth to eighth aspects of the invention, the albumin may be for use in a subject to which a therapeutic agent, especially a gene therapy vector is to be administered. Preferably the therapeutic agent is to be administered prior to, simultaneously with or subsequent to the administration of the albumin. The albumin is preferably for administration immediately prior to or simultaneously with the therapeutic agent. The therapeutic agent is preferably for the treatment of a disease of the brain or spinal cord, especially a disease of the brain. It may be a cancer, especially a cancer of white matter, in particular a glioma. Alternatively, it may be any other appropriate neurological disease, especially a white matter disease such as multiple sclerosis. The therapeutic agent may be gene therapy agent, especially a gene therapy vector. Alternatively, it may be pharmaceutical agent, such as a neurotrophic factor, especially glial cell derived neurotrophic factor (GDNF); an antibody or fragment thereof; an immunosuppressant; an immunomodulator, especially fingolimod; a cytokine, especially an interferon, such as interferon 1 alpha or beta; or an anti-inflammatory. The therapeutic agent, especially a gene therapy vector, is preferably for administration at a different, especially reduced dose compared with the usual therapeutically effective dose. The dose may be altered by reducing the actual dose given, or, when given by infusion, by reducing or increasing the flow rate of the agent, by diluting the infusate or by increasing or decreasing the time period over which the infusion is given.

Preferably the albumin is in isotonic solution, especially in a solution of artificial CSF. The artificial CSF is preferably as defined in the first aspect of the invention.

The subject is preferably a mammal, preferably a primate, especially a human. The subject is preferably suffering from cancer, especially a brain cancer, particularly glioma.

Preferably the compositions, albumin and gene therapy vectors are for administration to the brain, especially by infusion, most preferably via a fine catheter. In particular, the compositions, albumin and gene therapy vectors are for administration by convection enhanced delivery.

DETAILED DESCRIPTION OF THE INVENTION

The invention will now be described by way of example only, with reference to the following figures in which:

FIG. 1 shows the pig infusion device.

This device was constructed from a series of zirconia tubes (a). Inside these tubes there was a length of fused silica (outer diameter of 220 μm and an inner diameter of 150 μm) protruding 3 mm from the distal end. This fused silica extended proximally from the rigid cannula through a flexible length of tecothane tubing to the 3-way connector. FIG. 1b shows the cannula inserted through the stereo-guide of a Pathfinder stereotactic robotic arm, through a small burr-hole and into the brain. FIG. 1c demonstrates the 3-way connector attached to two glass Hamilton syringes placed in a syringe driver.

Figure 2:
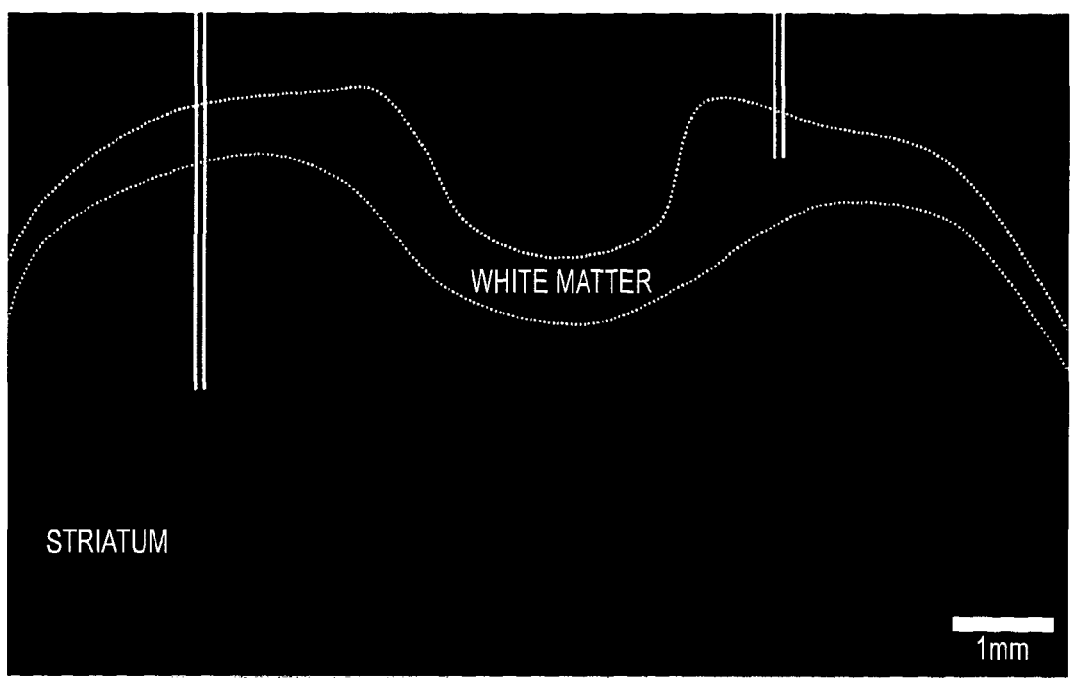

FIG. 2 shows Tissue Damage from HSV-1 Infusions.

Representative coronal histological section demonstrating damage in the striatum (left) and white matter (right) following an infusion of HSV-1. Solid white lines represent the trajectory and position of the infusion cannulae. Dotted white lines represent the boundaries between grey and white matter in the rat brain. The cortex lies above the top dotted white line. Below the lower dotted white line are the striata on each side of the lateral ventricles and the midline septum. There are a limited number of EGFP-positive cells in the margins of the damaged tissue.

Figure 3:
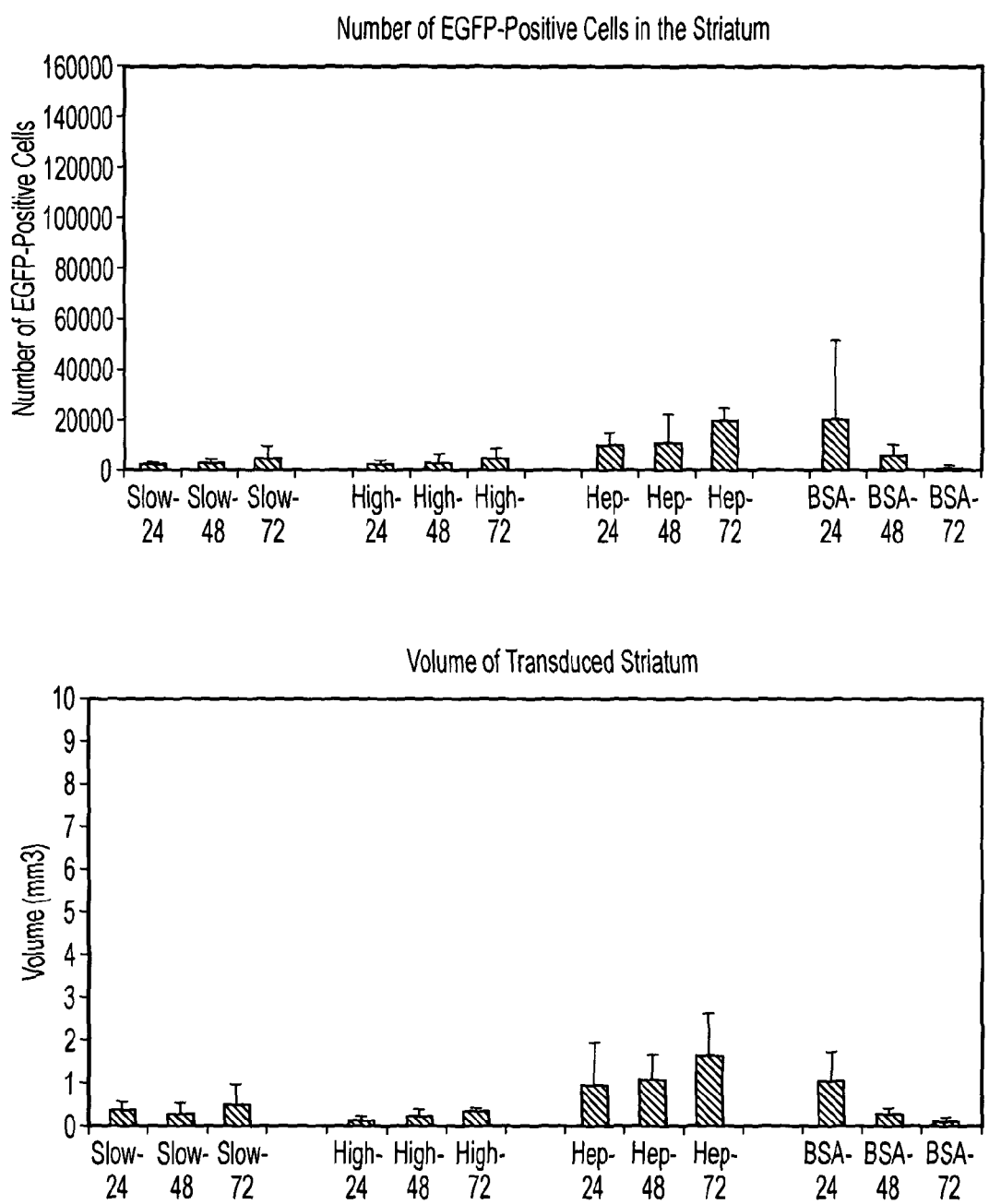
Figure 3:
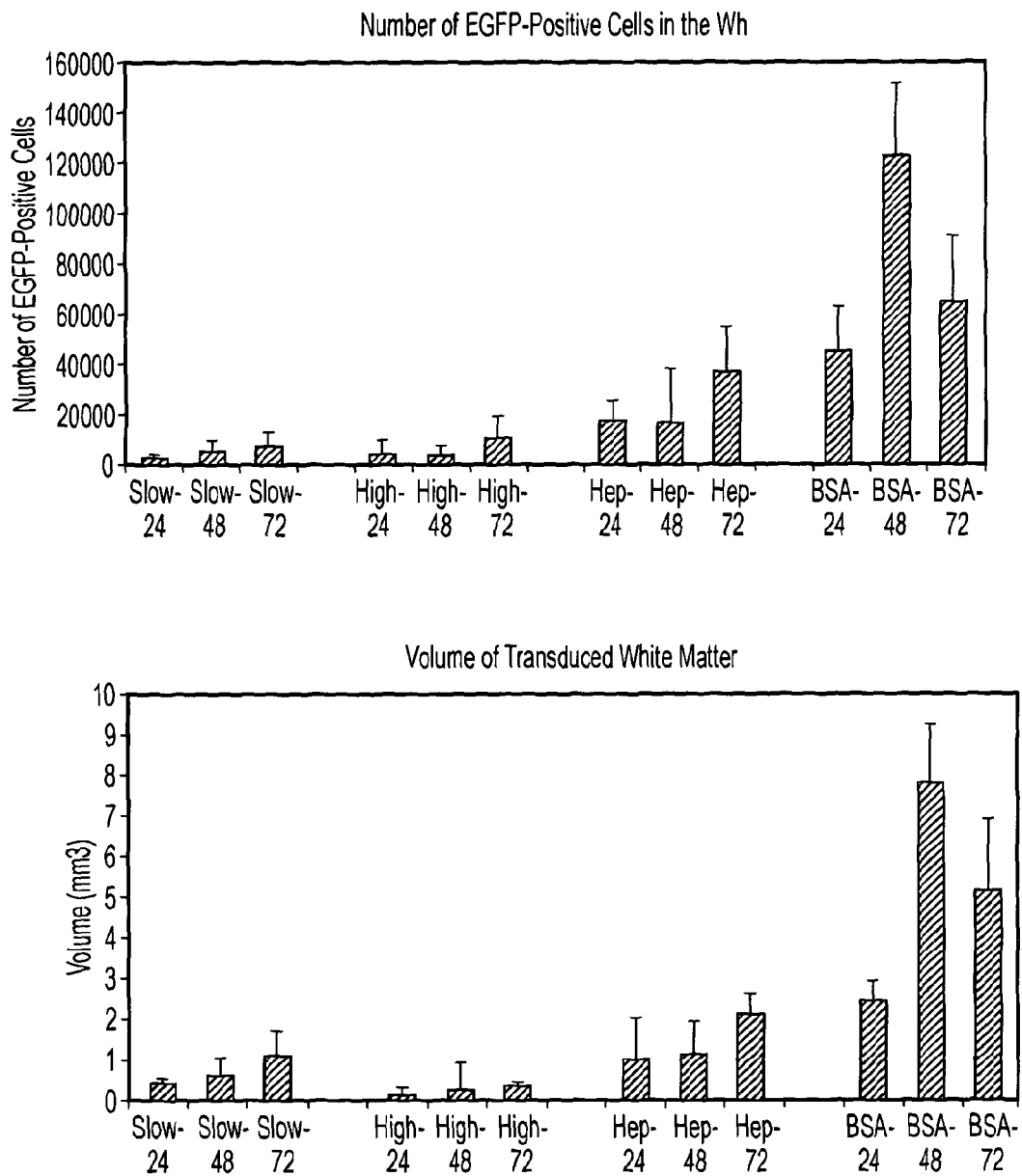

FIG. 3 shows HSV-1 Vector Distribution in Rat Striatum and White Matter.

Infusions of HSV-1 at a slow-rate (0.5 μl/min), a high-rate (2.50 μl/min), with heparin and following pre-infusion of the tissue with 1% BSA. Number of EGFP-positive cells 0.5 μl/min (p=0.012), 2.4 μl/min (p=0.013) (a) and volume of distribution of EGFP-positive cells 0.5 μl/min (p=0.019), 2.50 μl/min (p=0.011) (b) at 24, 48 and 72 hours. Number of EGFP-positive cells (c) and volume of distribution of EGFP-positive cells (d) at 24, 48 and 72 hours following infusion into the striatum. P values are compared to vector infusions in standard buffer.

Figure 4:

FIG. 4 shows Haemorrhage Associated with HSV and Heparin Co-infusion.

Haematoxylin and eosin stained coronal section demonstrating extensive haemorrhage following attempted CED-based co-infusion of HSV-1 and heparin into the striatum of a rat. The parallel dotted white lines represent the trajectory and location of the infusion cannula.

Figure 5:
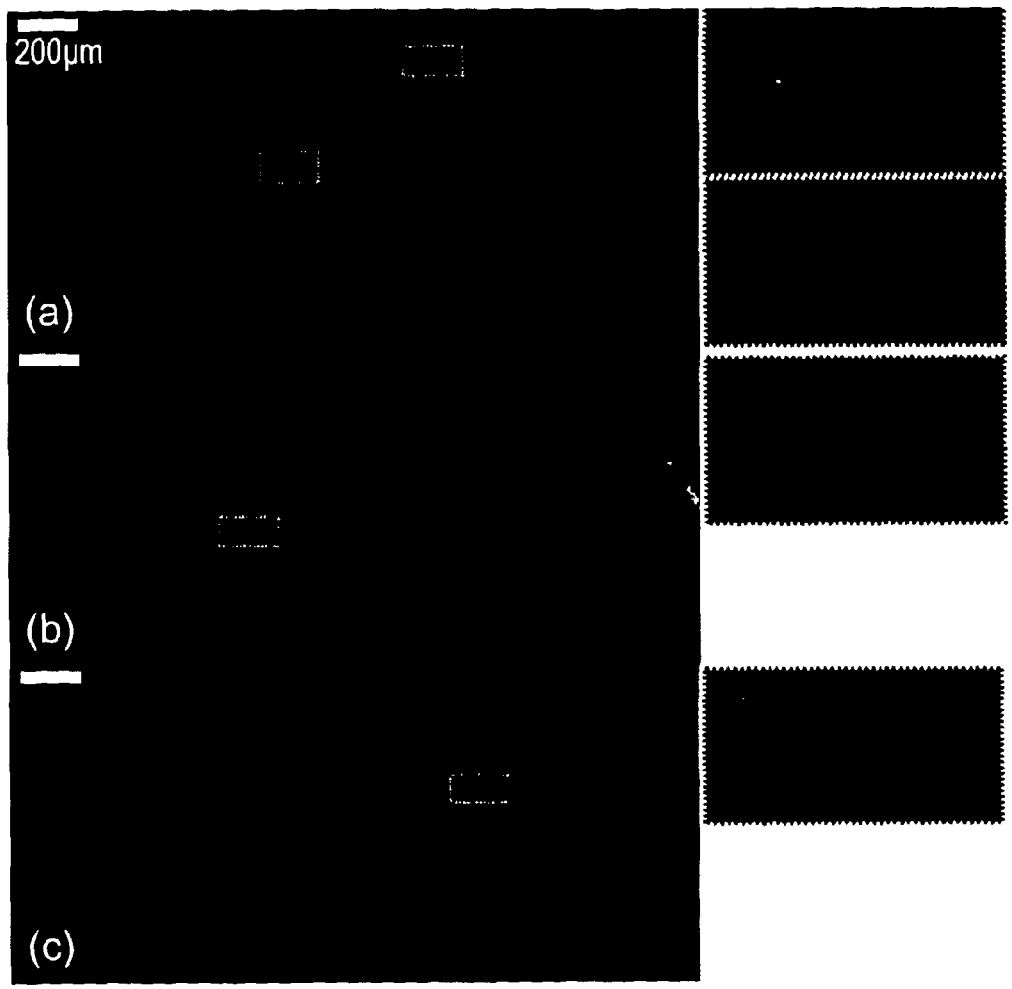
Figure 5:
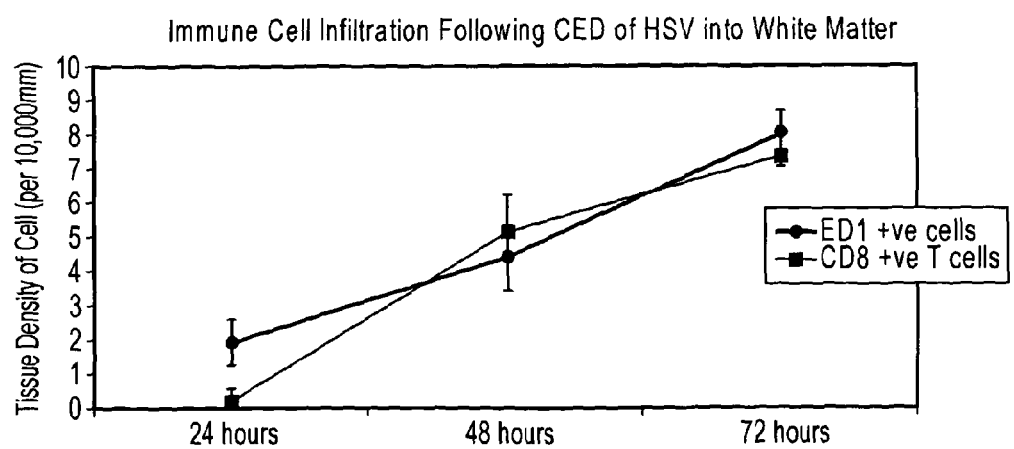

FIG. 5 shows Immune Cell Infiltration into HSV-1 Infused Rat White Matter.

Representative images showing widespread EGFP expression in the white matter (a), ED1-positive microglia (b) and CD8-positive T cell (c) infiltration into the white matter at 48 hours. Note the lack of obvious tissue damage in the white matter (white bars=200 μm). Outlined boxes show higher magnification images of representative areas. The graph demonstrates the rapid increase in ED1 and CD8-positive cell density in the brain following successful distribution of HSV-1 vectors through the white matter (d).

Figure 6:
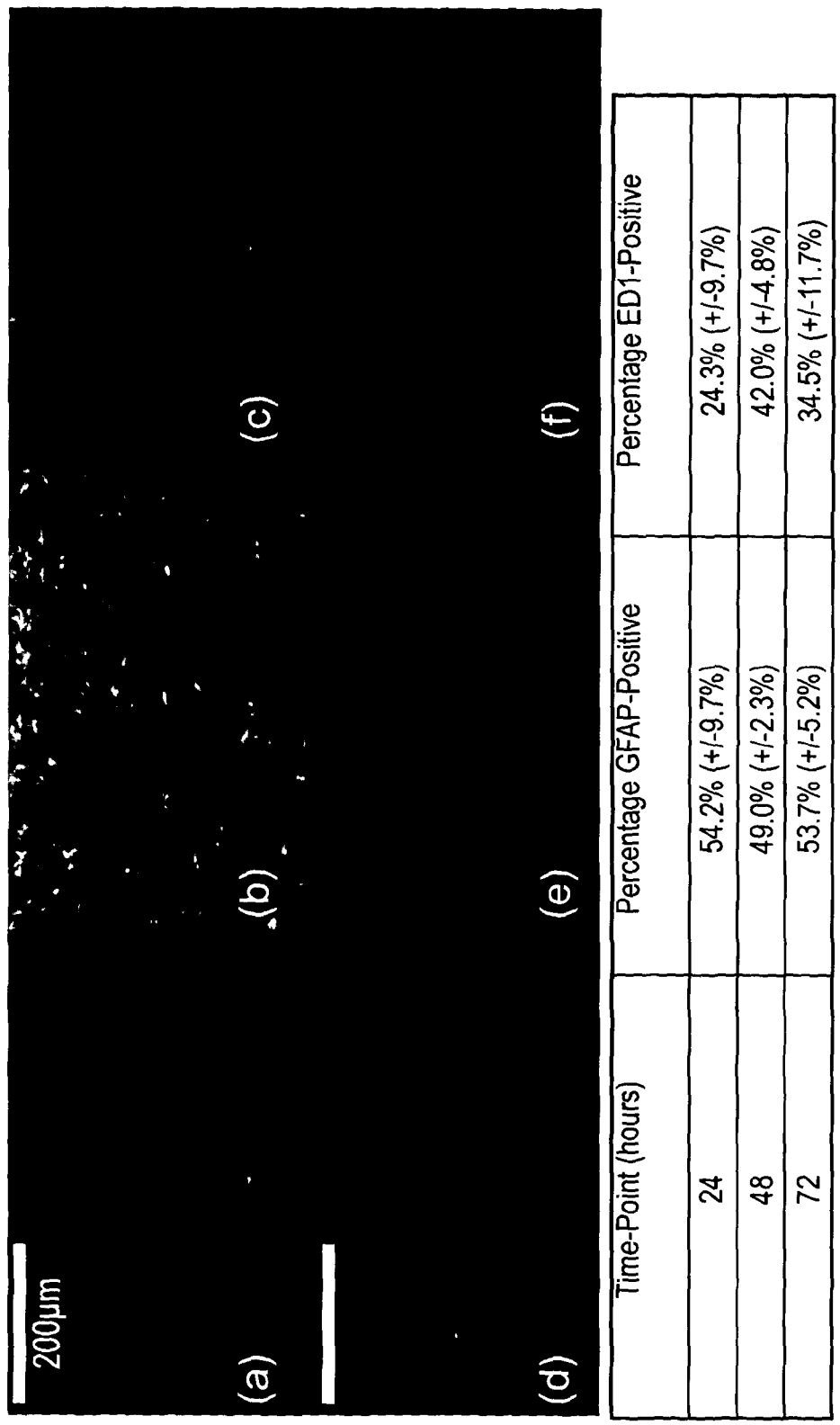

FIG. 6 shows Transductional Tropism of HSV-1 in Rat Corpus Callosum.

Representative images showing EGFP-expressing cells in the white matter (a) immunopositive for GFAP (b) and the colocalisation of EGFP and GFAP (c). EGFP expressing cells in the overlying cortex (d). A minority of transduced cells in the cortex colocalised with NeuN (e) and colocalisation of both EGFP and NeuN (f). The table shows the transductional tropism of HSV-1 in the white matter at 24, 48 and 72 hours (g).

Figure 7:
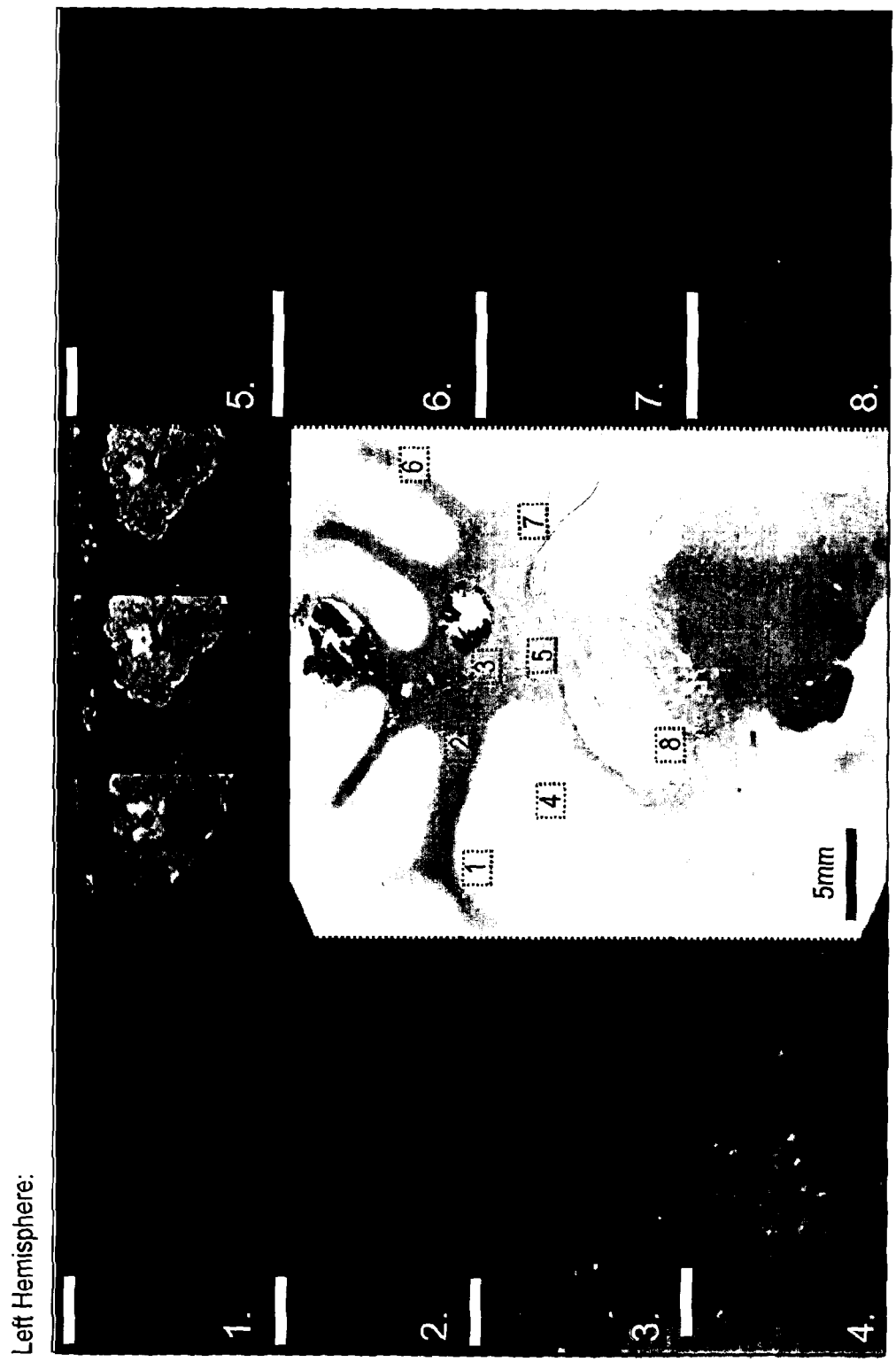

FIG. 7: HSV-1 Infusions into Pig Corona Radiata (Left hemisphere images).

Images demonstrate EGFP-positive cells throughout the corpus callosum, corona radiata and overlying cortex (a-g). EGFP-positive cells concentrated in the perivascular space around a vessel in the lentiform nucleus (h).

The central section is an unstained coronal histological section along the cannula track. There is a clearly visible haemorrhage at the site of the cannula-tip. T2-weighted coronal MR images (i-k) around the infusion site clearly show evidence of high signal extending through the corona radiata.

Figure 8:
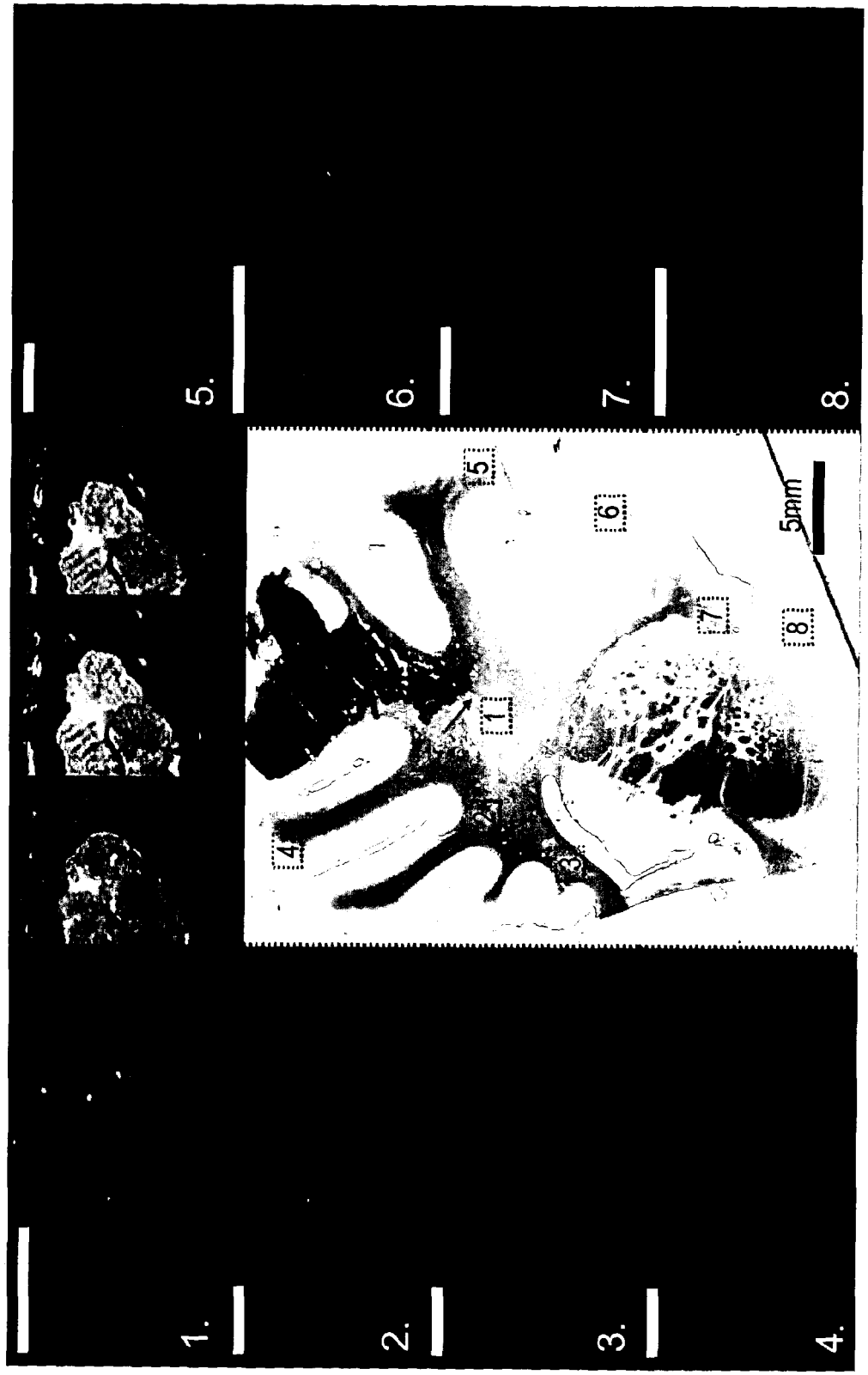

FIG. 8 HSV-1 Infusions into Pig Corona Radiata (Right hemisphere images).

The central section is an unstained coronal section along the cannula track. The location of the fused silica tip of the cannula is arrowed. Images 1 to 6 and 8 demonstrate widespread distribution of EGFP-positive cells in the corpus callosum, corona radiata and cortex (a-f, h). Extensive EGFP-positive cells concentrated in the perivascular space of a branch of the lenticulostriate arteries (g). T2-weighted coronal MR images show clear evidence of high signal extending throughout the corona radiata (i-k). (White scale bars represent 200 μm).

Figure 9:
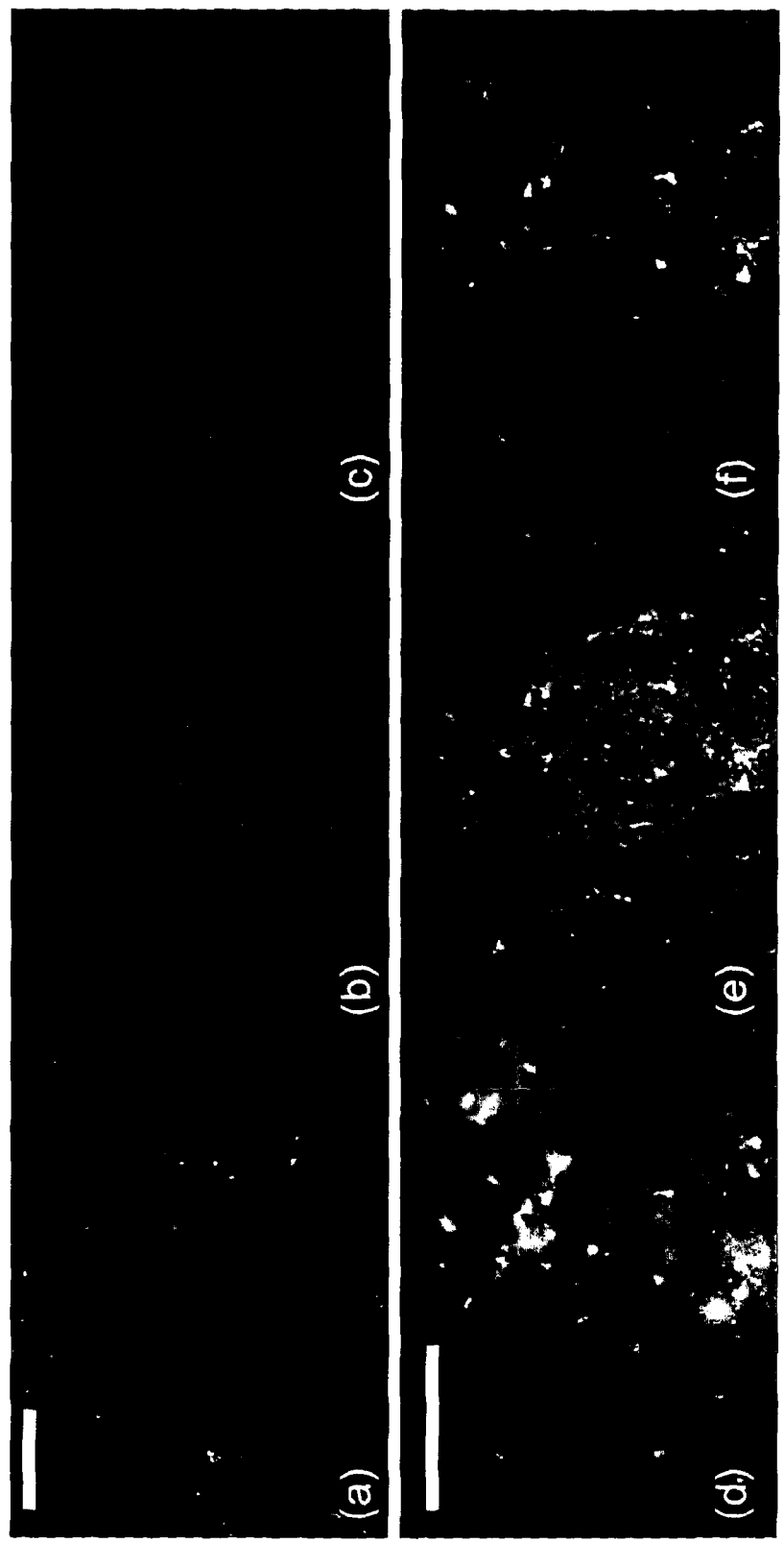

FIG. 9: Transductional Tropism of HSV-1 in Pig Corona Radiata.

Representative images showing EGFP-expressing cells in the pig corona radiata. The majority of these cells colocalised with markers for astrocytes (GFAP) or activated microglia (ED1). Representative photomicrograph of EGFP expressing cells (a), ED1 expressing cells (b) and overlay of EGFP and ED1 (c). Photomicrograph of EGFP expressing cells (d), GFAP (e) and overlay of EGFP and GFAP (f).

INTRODUCTION

Malignant gliomas are the most common primary brain tumour and are almost invariably incurable. Critical reasons for this include the highly infiltrative nature of these tumours, intrinsic tumour chemoresistance and the difficulty associated with achieving therapeutic concentrations of chemotherapeutics in the brain without causing toxicity. The direct intraparenchymal administration of oncolytic viral vectors by convection-enhanced delivery (CED) represents a promising new treatment strategy. However there is no evidence to suggest that oncolytic viruses as large as HSV-1 can be administered by CED. In this study, the ability to administer an HSV-1 viral vector have been evaluated in detail in the grey and white matter of both small (rat) and large (pig) animal models.

Infusions of an HSV-1 based vector expressing an EGFP reporter gene were undertaken into the striatum and corpus callosum of rats and the corona radiata of a pig using infusion parameters compatible with CED. The volume of distribution and number of transduced cells following each infusion were determined using stereological methods. Immunohistochemistry was employed to determine the transductional tropism of vectors and to evaluate for the presence of immune cell infiltration into the brain. Strategies to improve vector distribution were evaluated, including using high flow-rate infusions, co-infusing heparin or pre-infusing the tissue with an isotonic albumin solution.

HSV-1 infusions into rat grey and white matter at both slow (0.5 μl/min) and high infusion rates (2.5 μl/min) led to extensive tissue damage and negligible cell transduction. Co-infusion with a low concentration of heparin to minimise non-specific vector binding led to extensive haemorrhage. Pre-infusion of tissue with an isotonic albumin solution facilitated widespread vector distribution and cell transduction in white matter but did not improve vector distribution in grey matter. Using this approach in pig brain led to widespread vector distribution with extensive transduction of astrocytes and activated-microglia with transduced cells in the cortex and perivascular spaces distant to the infusion site. In rat brain, EGFP-expression peaked 48 hours after vector administration and was associated with a vigorous immune response characterised by infiltration of ED1-positive microglia and CD8-positive T cells.

Direct infusions of HSV-1 based viral vectors into the brain leads to minimal vector distribution, negligible cell transduction and extensive damage. Tissue pre-infusion with an isotonic solution prior to vector administration represents a practical and highly effective technique for achieving widespread vector distribution and should be adopted in ongoing and future clinical trials employing HSV-1 based viral vectors.

Methods

Vectors

HSV-1 viral constructs harbouring null mutations in the ICP4 and ICP27 genes, and expressing enhanced green fluorescent protein (EGFP) under the control of a CMV promoter were kindly provided by Biovex.

Vector Infusions

All procedures were carried out in accordance with UK Home Office animal welfare regulations and with appropriate Home Office licences.

Rat Infusion Apparatus and Procedures

Acute infusion cannulae were constructed from lengths of fused silica with an outer diameter of 220 μm and an inner diameter of 150 μm. These lengths of fused silica were connected to 10 μl Hamilton syringes via a connection device made in-house that served to create a seal between the chamber of the Hamilton syringe and the lumen of the fused silica, and which guided the fused silica cannula from the Hamilton syringe, through the dura and into the brain. The Hamilton syringe, with the cannula attached via this connector device, was then mounted in an infusion pump (World Precision Instruments Inc., Sarasota, Fla., USA) attached to a stereotactic frame (Stoelting Co, Wood Dale, Ill. USA) in which rats were immobilised. To insert a cannula, the entire pump/syringe/connector/cannula construct was lowered in the stereotactic frame until the target depth was reached.

Male Wistar rats (B & K, UK) were group-housed and allowed to acclimatize prior to experimental procedures. Male rats weighed 225 to 275 g were anaesthetised with an intraperitoneal dose of ketamine and xylazine and placed in a stereotactic frame (Stoelting Co, Wood Dale, Ill. USA). A linear incision was made between the glabella and the occiput and the skull exposed. Burr holes with a diameter of approximately 2 mm were placed 0.5 mm anterior and 2.75 mm lateral to the bregma and cannulae were inserted to a depth of 5 mm below the dura when the striatum was targeted and to a depth of 2 mm when the corpus callosum was targeted. All cannulae were pre-primed with vector prior to insertion into the brain. Every attempt was made to ensure that no air bubbles were present in the infusion cannula. All vector infusions were of 4 μl at a concentration $1 \times 10^7$ pfu/ml. Animals were subdivided into four groups based on the infusion parameters used (Table 1). Heparin co-infusion was achieved by mixing the viral infusate with 2 μl of 5000 IU/ml of heparin (10 IU of heparin). Bovine serum albumin (BSA; Sigma, UK) was mixed in sterile saline. BSA preinfusion of tissue was achieved by infusing 4 μl of isotonic 1% BSA into the striatum and corpus callosum immediately prior to vector infusion. Upon infusion completion, the cannula was left in situ for 5 mins prior to be removed at a rate of 1 mm/min. The wound was then closed with 4/0 vicryl, a dose of intramuscular buprenorphine was administered (30 μg/kg)) and the anaesthetic was reversed with a 0.1 mg/kg intraperitoneal dose of atipamezole hydrochloride (Antisedan; 200 μg/kg; Pfizer, Kent, UK).

Within each group, animals were sacrificed at 24, 48, 72 or 96 hour time-points by perfusion fixation under deep general anaesthetic with 100 mls of phosphate buffered saline followed by 100 mls of 4% paraformaldeyhde (pH 7.4). The brain was then removed from the skull and placed in 4% paraformaldeyhde (pH 7.4) for 48 hours and then cryoprotected in 30% sucrose prior to sectioning.

Pig Infusion Apparatus and Procedures

A male Large White Landrace pig weighing 45 kg was administered an intramuscular dose of ketamine (0.1 mg/kg body weight). General anaesthesia was then induced and maintained with isoflurane (2-5%) and the animals intubated with a cuffed endotracheal tube. Intravenous access was obtained using a cannula placed in an ear vein and normal saline was infused at a rate of 250 ml/hr.

Pig head fixation was achieved using a custom-built fixation device incorporating bilateral MRI-compatible zygomatic screws, a mouldable palate tray and snout-strap. All materials were fully MR-compatible to prevent imaging artefact. Following robust pig head fixation, an arc of fiducials was placed over the animal's head. Flex-L coils were then attached to the lateral aspects of the head and the animal was transferred to a 1.5T MRI scanner (Intera, Phillips). Stereotactic surgical planning and procedures were undertaken using a Pathfinder (Prosurgics, UK) stereotactic robotic arm and associated software. Briefly, this stereotactic arm functioned as follows. The pig was imaged with an array of fiducial balls placed in a fixed location over the animal's head. In theatre, the fiducial balls were replaced with optical reflector balls placed into precisely the same locations. The location of the reflector balls were visualised using a camera in the underside of the robotic arm. The optical reflector balls and MRI fiducials were co-registered automatically by the planning software. The software only allowed visualisation of MR images from a single plane. Consequently as coronal images facilitated the best views of the planned cannula trajectory, they were used for all surgical planning. To conduct the surgical procedure, a range of end-effectors designed to accommodate the burr hole generation and cannula delivery tooling were placed onto the robotic arm.

An acute delivery cannula for vector infusions was developed, which incorporated a fused silica tube (outer diameter of 220 µm and an inner diameter of 150 µm) supported along its distal length by a rigid zirconia tube. To facilitate the preinfusion of tissue with 1% BSA prior to infusing virus, a fused silica-lined 3-way connector was developed so that two syringes could be attached directly to the fused silica tube of the acute cannula (FIG. 1). This ensured that the cannula could be inserted into the corona radiata and then infusions of BSA and virus performed without the need to remove the cannula to reload it with virus. Infusions of 80 µl of vector ($1 \times 10^7$ pfu/ml) were undertaken into the corona radiata of each hemisphere as follows:

Left Hemisphere:

The cannula was inserted 8 mm short of target and a 1% BSA preinfusion performed at 1 µl/min for 2 mins, 2.5 µl/min for 2 mins and then 5 µl/min for 7 mins (total BSA volume of 42 µl). Vector was then infused at a rate of 5 µl/min for 8 mins (total vector volume of 40 µl). The cannula was then inserted to target and the BSA preinfusion repeated at 1 µl/min for 2 mins, 2.5 µl/min for 2 mins and then 5 µl/min for 4 mins (total BSA volume of 42 µl). Vector was then infused at a rate of 5 µl/min for 8 mins (total vector volume of 40 µl).

Right Hemisphere:

The cannula was inserted to target and a 1% BSA preinfusion performed at 1 µl/min for 2 mins, 2.5 µl/min for 2 mins and then 5 µl/min for 7 mins (total BSA volume of 420). 80 µl of vector was then immediately infused at a rate of 5 µl/min for 16 mins (total vector volume of 80 µl).

Following infusion completion, the cannula was left in place for 10 mins prior to being withdrawn slowly by hand. CSF leakage from the burr hole and cannula track was sealed with Cerebond prior to wound closure. The animals were then transferred back to the MRI scanner and T2-weighted imaging performed to confirm that cannulae had been accurately inserted to target. Animals were recovered for a period of 28 days, before being killed by perfusion fixation under terminal anaesthesia and the brains harvested for histological analysis.

Histology

Rat brains were cut into 35 µm thick coronal sections using a Leica CM1850 cryostat (Leica Microsystems, Germany). Pig brains were cut into 100 µm coronal sections using a Leica SM2500 microtome. Immunohistochemistry was performed on selected sections. Briefly, all solutions for immunohistochemistry were made in phosphate buffered saline (PBS). Free-floating PFA-fixed sections were washed 3 times for 15 minutes in PBS and incubated in 3% hydrogen peroxide to remove endogeneous peroxidise activity. Sections were then washed 3 times for 15 minutes in PBS, before being blocked for 1 hour in blocking solution (10% normal goat or donkey serum) room temperature. Sections were then transferred directly from blocking solution into primary antibody, appropriately diluted in blocking solution, and incubated overnight. The following primary antibodies were used: mouse anti-NeuN (1:300; Chemicon, UK), rabbit anti-GFAP (1:200; Chemicon), mouse anti-ED1 (1:100; Serotec, UK), mouse anti-CD4 (Ox38) (1:300; Serotec, UK) and mouse-anti CD8 (ox 8) (1:300; Serotec, UK. After three PBS washes, sections were then incubated with secondary antibody for at least 2 hrs at room temperature. For fluorescence immunohistochemistry, species-specific secondary antibodies (Cy3) were used (1:200; Jackson Laboratories, CA, USA). After PBS washes, sections were mounted in Vectashield (Vectorlabs, CA, USA) on gelatin-coated slides and coverslipped, prior to fluorescent imaging.

Imaging

Fluorescent imaging was undertaken using a Leica DM5500 microscope (Leica Microsystems, Germany) and digital camera (Microbrightfield, USA). Stereological counts were undertaken on immunostained sections using commercially-available software (Stereoinvestigator, Microbrightfield). Briefly, population estimates were undertaken on representative tissue sections to determine the counting frame size, counting frame number and number and separation of tissue sections necessary to achieve an accurate cell count with a Gundersen (m=1) coefficient of error of less than 0.1. Using these parameters, cell counts were then undertaken on serial sections of a uniform distance apart using the Optical Fractionator probe. The volume of distribution of transduced cells was calculated by tracing contours around the outer margins of the EGFP-expressing cells on each section. Transduced cells outside the striatum were excluded from these contours to ensure that only the intrastriatal volume of distribution of transduced cells was calculated. Infusions that were associated with obvious leakage of vector into the ventricular system were excluded from further analysis. Determination of the vector cell tropism and the density of activated microglia and CD4 and CD8 positive T-lymphocytes in the volume of viral distribution for each infusion was performed on selected tissue sections close to the needle-track using the Fractionator probe.

Statistical Analysis

Tukey's test was used in conjunction with analysis of variance (ANOVA) to determine whether there was a significant difference in vector distribution and cell transduction associated with different infusion parameters.

Results

HSV Infusion into Rat Striatum and White Matter

Infusions of HSV-1 into both the striatum and white matter of rats at a flow-rate of 0.5 μl/min were associated with extensive tissue damage and transduction of a negligible number of cells in close proximity to the infusion site (FIG. 2). In an attempt to improve the volume of distribution and number of transduced cells, infusions were repeated at a higher flow-rate (2.5 μl/min) in order to increase the pressure achieved at the cannula-tip. However, a similar pattern of extensive tissue damage with low levels of cell transduction and poor distribution of virally-transduced cells was observed.

It was hypothesised that the poor distribution of virally-transduced cells and extensive tissue damage associated with HSV infusions were caused by aggregation of viral particles in the tissue immediately around the cannula-tip or due to the comparatively large viral particles (diameter of approximately 250 μm) being forced into the narrow extracellular space. Consequently two strategies were developed to test these hypotheses. In an attempt to minimise extensive viral binding around the cannula-tip, infusions were repeated in a heparin solution. Although there was an increase in the number of transduced cells and the volume of distribution of virally-transduced cells in the presence of heparin compared to infusions of vector (in standard buffer) at 0.5 μl/min and 2.50 μl/min, this was not statistically significant (FIGS. 3a and b). In contrast, preinfusion of white matter with an isotonic solution of 1% bovine serum albumin (BSA), immediately prior to viral infusion led to a significant increase in both the number of cells transduced and the volume of distribution of transduced cells, both of which peaked 48 hours after the infusion (FIGS. 3a and b). Compared to vector infusions (in standard buffer) at 0.50 μl/min and 2.50 μl/min this effect was statistically significant for both the number of transduced cells (p=0.012 and p=0.013 respectively) and the volume of distribution of transduced cells (p=0.019 and p=0.011 respectively). This effect was not observed in the striatum. FIG. 4 shows haemorrhage associated with HSV and Heparin Co-infusion thus rendering this approach clinically unfeasible.

Immune Cell Infiltration into the White Matter Following Successful HSV Infusions Preinfusion of the white matter with 1% BSA enabled widespread cell transduction without significant infusion-related tissue damage (FIG. 5a). The number of EGFP-positive cells and volume of distribution of EGFP-positive cells peaked at 48 hours. Widespread distribution of HSV-1 viral particles in the white matter did however result in a rapid infiltration of both ED1-positive microglia (FIG. 5b) and CD8-positive T cells (FIG. 5c) which increased between 24 and 72 hours (FIG. 5d).

Transductional Tropism of HSV-1 in the White Matter

Effective HSV-1 distribution in the white matter, following tissue preinfusion with 1% BSA, led to widespread transduction of GFAP-positive astrocytes (FIGS. 6a, b and c). Although not included in the analysis of the number of transduced cells and volume of distribution of transduced cells in the white matter, cells were also transduced in the overlying cortex. Morphologically the majority of these cells were astrocytes although some of these cells colocalised with the neuronal marker NeuN (FIGS. 6d, e and f). The majority of cells transduced in the white matter colocalised with GFAP, although a significant proportion of ED1-positive activated microglia were also transduced (Table in FIG. 6). There was no significant difference in the percentage astrocytic or microglial cell transduction between 24 and 72 hours.

Pig Infusions of HSV

Having determined that tissue preinfusion with 1% BSA enabled widespread HSV-1 vector distribution in the white matter of rats, the practicality of this approach was evaluated over much larger volumes of brain in a pig model. Infusion into the left hemisphere was performed at two sites along the catheter trajectory within the corona radiata, whereas in the right hemisphere the entire viral solution was infused at a single site in the corona radiata. The animal was recovered for 2 days and demonstrated no abnormal neurological signs in that time.

On the left side, the proximal infusion was not associated with damage at the cannula-tip. In contrast, the infusion at the distal target site resulted in a small haemorrhage with a diameter of approximately 3 mm. (FIG. 7, central panel). In spite of this damage, widespread distribution of EGFP-positive cells was observed through the corona radiata and in distant sites in the frontal cortex, corpus callosum and insula (FIG. 7a-g). Furthermore EGFP-positive cells were seen to be localised in perivascular spaces very distant from the infusion-site, particularly in the vicinity of the lenticulostriate arteries. Excluding EGFP-positive cells confined to perivascular spaces, transduced cells were observed in the brain parenchyma up to 15 mm from the infusion site. T2-weighted coronal MR images (FIGS. 7i-k) around the infusion site clearly show evidence of high signal extending through the corona radiata and, in addition, the haemorrhage area.

The infusion in the right hemisphere was not associated with damage at the cannula tip (FIG. 8, central panel). Widespread distribution of EGFP-positive cells was observed in the corona radiata and overlying cortex and as far as the corpus callosum and the cortex of the temporal lobe (FIG. 8a-f, h). As in the left hemisphere, EGFP-positive cells were present in the perivascular spaces around branches of the lenticulostriate arteries (FIG. 8g).

T1-weighted MR images of the infusions showed extensive areas of high-signal in the corona radiata. Histologically, all of the areas of high-signal corresponded with areas of virally-transduced tissue. However, EGFP-expressing cells were also present far beyond the boundaries of regions of high-signal, although it is feasible that the transduction of cells distant to the infusion sites may have resulted from axonal or perivascular transport of infused vector, rather than CED.

FIG. 9 shows the immune response elicited by HSV-1 transduced cells in the pig corona radiata. Transduced cells expressing EGFP co-localised with ED1 (FIG. 9a-c) which shows the presence of CD68-expressing microglia and, in addition, GFAP (FIG. 9d-f).

Discussion

High-grade gliomas are highly infiltrative tumours. Whilst the main tumour mass can often be treated effectively with surgery and/or radiotherapy, destroying the infiltrating tumour cells is technically challenging. For vector-mediated oncolysis to prove efficacious there is an overwhelming requirement to transduce as many tumour cells as possible on initial vector administration. However, as these tumours contain significant areas of necrosis, direct intratumoural vector delivery is unlikely to be effective and is therefore not the focus of this study. This is reflected in the failure of previous clinical trials to demonstrate convincing evidence of efficacy in the treatment of high-grade gliomas (7-9). Indeed, the focus of a more recent study has been to administer replication-selective HSV vectors into the peritumoural tissue (6). As it is possible to achieve widespread vector distribution in the brain by CED it represents the most rational approach for the delivery of oncolytic replication-selective vectors in clinical practice. However, it was questionable whether HSV-based vectors, with a diameter of between 120 and 300 nm (Jacobs et al, 1999) could be infused through the brain extracellular space, which has a diameter of up to 80 nm (Thorne and Nicholson, 2006). In this study, the feasibility of administering a replication-selective HSV-1 vector by CED into normal brain was therefore examined in detail. In spite of the large number of preclinical studies that have involved the direct intracranial administration of HSV-based vectors (17, 18, 20-24, 26-41) remarkably this represents the first published study to evaluate the distribution properties of an HSV-1 vector using appropriate infusion parameters in both grey and white matter, as well as evaluation of strategies to improve vector distribution.

Considering the discrepancy in size between the brain extracellular space and the diameter of HSV-1 particles, it was unsurprising that vector infusions at 0.5 µl/min led to extensive tissue damage in both the grey and white matter and there was minimal penetration of vector into the tissue. In view of this damage, it was hypothesised that an infusion at a higher flow-rate and therefore higher pressure might improve vector distribution by expanding the brain extracellular space. However, similar levels of tissue damage were observed and vector distribution was poor. This tissue damage draws parallels with post-mortem observations made by Rampling et al (2000), who found cystic cavities at the infusion site in the brain of two patients who had HSV1716 injected intratumourally.

Heparan sulphate proteoglycans are known to act as cell surface receptors for HSV-1 (WuDunn and Spier, 1989; Shieh et al, 1992) as well as a number of other viruses including serotype 2 recombinant adeno-associated virus (rAAV2). Indeed co-infusion of heparin has been shown to improve the distribution of rAAV2 in the striatum of adult rats, presumably by competitive antagonism of viral binding to heparan sulphate proteoglycans (Nguyen et al, 2001). Furthermore, Mastakov et al (2002a) demonstrated that heparin co-infusion at concentrations of between 500 and 5000 IU/ml significantly improved the distribution of reporter gene transfer, although higher concentrations were associated with fatal intracerebral haemorrhages. However to date co-infusions of HSV-1 and heparin have not been reported.

In this study, co-infusion of HSV at a concentration of 5000 IU/ml led to a slight increase in the distribution of EGFP expression, although animals did develop clinically undetectable, but extensive intracerebral haemorrhages in both the grey and white matter. In view of the widespread damage associated with infusions of HSV-1 in the absence of heparin, it is unsurprising that the co-infusion of heparin led to this extensive bleeding. As such this approach is unlikely to be of significant value in clinical practice.

A number of studies have evaluated the CED-based distribution properties of nanoparticles of a similar size to HSV-1. Chen et al (2005) and MacKay et al (2005) demonstrated that polystyrene nanoparticles and liposomes with a diameter of 200 nm only penetrated short distances into the striatum of rats. Interestingly however, Chen et al (2005) demonstrated that coating the nanoparticles with albumin to shield the hydrophobic particle surface significantly improved their distribution. Furthermore, Neeves et al (2007) demonstrated that preinfusing the striatum with isotonic saline significantly improved the distribution of 53 nm diameter polystyrene nanoparticles in the striatum of rats. This effect was greater than was observed with pre-infusion of hyaluronidase to degrade the brain extracellular matrix, or hyperosmotic mannitol to osmotically expand the extracellular space.

In this study, the use of albumin pre-treatment to shield non-specific binding and achieve isotonic expansion of the brain extracellular space were amalgamated to facilitate the administration of a replication-selective HSV-1 vector. This approach facilitated the widespread distribution of vector in the white matter of rat and pig brain, although it was unsuccessful in the grey matter of rats. Nevertheless, these results clearly demonstrate that with appropriate tissue preinfusion, very widespread vector distribution is possible within the white matter. The main advantage of using a pig model was that these animals have a large gyrencephalic brain that is larger that that of many primates and can accommodate large volume infusions with drug-delivery cannulae of a scale that can be translated directly into human studies. Indeed it is our intention to utilise this cannula system in future clinical trials.

The ability to distribute HSV in white matter and not grey matter probably relates to the greater elasticity of white matter and subsequently its greater capacity to accommodate an infused volume (Bobo et al, 1994). Indeed the microstructural orientation of myelinated axons has been shown to be preserved via oligodendroglial processes in the presence of experimentally induced dilatation of the brain extracellular space (Marmarou et al, 1980). As a consequence, whilst pre-infusion of white matter with an isotonic albumin solution enables widespread vector distribution, it may not be feasible to use this approach to adequately target tumour cells that have arisen within or infiltrated into grey matter structures. Interestingly however, there was clear evidence of transduced cells in the cortex of pigs following vector infusion into the corona radiata. In view of the inability of HSV to distribute through grey matter in rat brain, it seems likely that cortical cell transduction occurred by axonal or perivascular transport of vector from the infusion site. As it seems unlikely that HSV could efficiently transduce myelinated axons in the white matter and in view of the observed distribution of transduced cells in the perivascular spaces, the latter of these two mechanisms seems most likely.

Successful distribution of vector within the white matter resulted in a brisk immune response characterised by a rapid infiltration of activated microglia and CD8-positive T cells. However, there is some evidence that ED1 is also a marker for neutrophils in ischaemic and traumatic brain injuries (41) and therefore the true identity of these infiltrating cells may merit further examination. In the context of treating brain tumours, the induction of an anti-HSV CD8 response may have the added benefit of enhancing the tumour cell kill (Todo et al, 1999). However, although no animals developed detectable neurological deficits, the long-term consequences of widespread distribution and cell transduction with HSV-1 vectors within the brain and the resultant vigorous immune response requires careful evaluation. This necessity is emphasised by the potential for significant vector escape from the relatively immune-privileged brain and into the systemic circulation with the subsequent development of an adaptive immune response. Realistically this could be mediated through tissue damage associated with cannula implantation, infusion-related damage or drainage of vector along the perivascular spaces. This is particularly significant as although antigen-presenting dendritic cells are not present in the uninflamed brain, dendritic cells are present in the perivascular space and CSF, into which the perivascular space drains (McMahon et al, 2006).

The potential risks of viral vector leakage into the CSF and the development of an immune response emphasise the importance of visualising vector distribution clinically. As such, a number of T1 and T2 contrast agents have been developed to act as surrogate markers of vector distribution (Szerlip et al, 2007; Fiandaca et al, 2008). However co-infusion of vector with a surrogate marker adds significant complexity and regulatory hurdles to the clinical administration of gene therapy vectors to the brain. In this study T2-weighted MR imaging was undertaken in an attempt to visualise infusion-related oedema. These images clearly demonstrated an area of high-signal in the vicinity of the infusions, which histologically corresponded with the location of transduced cells in the white matter, although cell transduction clearly extended beyond the margins of this high-signal. However, in view of the apparent perivascular and possible axonal transport of vector augmenting the distribution achieved directly by CED, it is highly unlikely that the use of surrogate markers or MR imaging would offer a realistic prediction of the final distribution of HSV vector-mediated transduced cells.

In summary, evidence from this study suggests that HSV-1 vectors are too large to be efficiently distributed by CED unless the target tissue is pre-infused to dilate the brain extracellular space. This finding has critical implications in interpreting the results of clinical trials involving the use of HSV-based viral vectors to treat patients with brain tumours. Indeed this data suggests that the infusion methods employed in these trials would have probably led to negligible vector distribution. Utilising this finding in future clinical trials however has the potential to improve patient outcome by maximising the number of transduced tumour cells and therefore maximise to possibility of treatment efficacy.

References

Bobo R. H., Laske D. W., Akbasak A., Morrison P. F., Dedrick R. L., Oldfield E. H. (1994). Convection-enhanced delivery of macromolecules in the brain. *Proc Nat Acad Sci, USA.*, 91(6): 2076-80.

Bowers W. J., Olschowska J. A., Federoff H. J. (2003). Immune responses to replication-defective HSV-1 type vectors within the CNS: implications for gene therapy. *Gene Ther* 10: 94105.

Canoll P., Goldman J. E. (2008). The interface between glial progenitors and gliomas. *Acta Neuropathol.*, 116: 465-77.

Chen M. Y., Hoffer A., Morrison P. F., Hamilton J. F., Hughes J., Schlageter K. S., Lee J., Kelly B. R., Oldfield E. H. (2005). Surface properties, more than size, limiting convective distribution of virus-sized particles and viruses in the central nervous system. *J Neurosurg.*, 103(2): 311-9.

Dempsey M. F., Wyper D., Owens J., Pimlott S., Papanastassiou V., Patterson J., Hadley D. M., Nicol A., Rampling R., Brown S. M. (2006). Assessment of 123I-FIAU imaging of herpes simplex viral gene expression in the treatment of glioma. *Nucl Med. Comm.*, 27(8): 611-7.

Fiandaca M. S. Varenika V., Eberling J., McKnight T., Bringas J., Pivirotto P., Beyer J., Hadaczek P, Bowers W., Park J., Federoff H., Forsayeth J., Bankiewicz K. S. (2009). Real-time MR imaging of adeno-associated viral vector delivery to the primate brain. *Neuroimage*, 47 Suppl 2:T27-35.

Harrow S., Papanastassiou V., Harland J., Mabbs R., Petty R., Fraser M., Hadley D., Patterson J., Brown S. M., Rampling R. (2004). HSV1716 injection into the brain adjacent to tumour following surgical resection of high-grade glioma: safety data and long-term survival. Gene Therapy, 11: 1648-58.

He B., Gross M., Roizman B. (1997). The $\gamma_1 34.5$ protein of herpes simplex virus 1 complexes with protein phosphatise $1\gamma$ to dephosphorylate the $\gamma$ subunit of the eukaryotic translation initiation factor 2 and preclude the shutoff of protein synthesis by double-stranded RNA-activated protein kinase. *PNAS.* 94: 843-8.

Hess C. F., Schaaf J. C., Kortmann R. D, Schabet M., Bamberg M. (1994). Malignant glioma: patterns of failure following individually tailored limited volume irradiation. *Radiother Oncol.*, 30:146-9.

Jacobs A., Breakefield X. O., Fraefel C. (1999). HSV-1 based vectors for gene therapy of neurological diseases and brain tumours: part II. Vector systems and applications. *Neoplasia*, 1(5): 402-16.

Louis D. N. (2006). Molecular pathology of malignant gliomas. *Ann Rev Pathol Mech Dis.*, 1:97-117.

Mackay J. A., Deen D. F., Szoka F. C. (2005). Distribution in brain of liposomes after convection enhanced delivery: modulation by particle charge, particle diameter, and presence of steric coating. *Brain Res.*, 103: 139-53.

Markert J. M., Medlock M. D., Rabkin S. D., Gillespie G. Y., Todo T., Hunter W. D., Palmer C. A., Feigenbaum F., Tornatore C., Tufaro F., Martuzo R. L. (2000). Conditionally replicating herpes simplex virus mutant, G207 for the treatment of malignant glioma: results of a phase 1 trial. *Gene Therapy*, 7: 867-74.

Marmarou A., Takagi H., Shulman K. (1980) in *Brain Edema*, Eds. Cervos-Navarro J., and Ferszt R. (Raven, New York). 28; 345-58.

Mastakov M. Y., Baer K., Kotin R. M., During M. J. (2002). Recombinant adeno-associated virus serotypes 2- and 5-mediated gene transfer in the mammalian brain: Quantitative analysis of heparin co-infusion. *Mol. Ther.* 5(4); 371-380.

McMahon E. J., Bailey S. L., Miller S. D. (2006). CNS dendritic cells: Critical participants in CNS inflammation? *Neurochem Int.*, 49(2): 195-203.

Morrison P. F., Laske D. W., Bobo H., Oldfield E. H., Dedrick R. L. (1994). High-flow microinfusion: tissue penetration and pharmacodynamics. *Am J. Physiol.*, 35: 8292-305.

Neeves K. B., Sawyer A. J., Foley C. P., Saltzman W. M., Olbricht W. L. (2007). Dilation and degradation of the brain extracellular matrix enhances penetration of infused polymer nanoparticles. *Brain Res.*, 1180: 121-32.

Nguyen J. B., Sanchez-Pernaute R., Cunningham J., Bankiewicz K S. (2001). Convection-enhanced delivery of AAV-2 combined with heparin increases TK gene transfer in the rat brain. *Neuroreport*, 12(9): 1961-4.

Papanastassiou V., Rampling R., Fraser M., Petty R., Hadley D., Nicoll J., Harland J., Mabbs R., Brown M. (2002). The potential for efficacy of the modified (ICP34.5') herpes simplex virus HSV 1716 following intratumoural injection into human malignant glioma: a proof of principal study. *Gene Therapy*, 9: 398-406.

Rampling R., Cruickshank G., Papanastassiou V., Nicoll J., Hadley D., Brennan D., Petty R., MacLean A., Harland J., McKie E., Mabbs R., Brown M. (2000). Toxicity evaluation of replication-competent herpes simplex virus (ICP34.5 null mutant 1716) in patients with recurrent malignant glioma. *Gene Therapy*, 7(10): 859-66.

Shah A. C., Benos D., Gillespie G. Y., Markert J. M. (2003). Oncolytic viruses: clinical application as vectors for the treatment of malignant gliomas. *J Neuroncol.*, 65: 203-26.

Shieh M. T., WuDunn D., Montgomery R. I., Esko J. D., Spear P. G. (1992). Cell surface receptors for herpes simplex virus are heparan sulfate proteoglycans. *J. Cell Biol.*, 116: 1273-81.

Szerlip N. J., Walbridge S., Yang L., Morrison P. F., Degen J. W., Jarrell S. T., Kouri J., Kerr P. B., Kotin R., Oldfield E.

H., Lonser R. R. (2007). Real-time imaging of convection-enhanced delivery of viruses and viral-sized particles. *J Neurosurg.*, 107(3): 568-77.

Thorne R. G., Nicholson C. (2006). In vivo diffusion analysis with quantum dots and dextrans predicts the width of brain extracellular space. *Proc Natl Acad Sci USA.*, 105(24): 8416-21.

Todo T., Rabkin S. D., Sundaresan P., Wu A., Meehan K. R., Herscowitz H. B., Martuza R. L. (1999). Systemic antitumor immunity in experimental brain tumor therapy using a multimutated, replication-competent herpes simplex virus. *Hum Gene Ther.* 10(17): 2741-55.

World Health Organization Classification of Tumours of the Nervous System, Editorial and Consensus Conference Working Group (2007). Louis, D N, Ohgaki, H, Wiestler, OD, Cavenee, WK (Eds), IARC Press, Lyon, France.

Wrensch M., Minn Y., Chew T., Bondy M., Berger M. S. (2002). Epidemiology of primary brain tumours: Current concepts and review of the literature. *Neuro Oncol.*, 4(4): 278-99.

WuDunn D. and Spier P. G. (1989). Initial interaction of herpes simplex virus with cells is binding to heparan sulfate. *J. Virol.* 63; 52-8.

TABLE 1

Summary of HSV-1 Rat Infusions

| Number | Group | Flow-Rate (□l/min) | Recovery Time (hours) | Co-infusion |
|---|---|---|---|---|
| 2 | Low-Flow | 0.5 | 24 | — |
| 2 | | | 48 | |
| 2 | | | 72 | |
| 2 | High-Flow | 2.5 | 24 | — |
| 2 | | | 48 | |
| 2 | | | 72 | |
| 2 | Heparin | 0.5 | 24 | 10 units of |
| 2 | | | 48 | heparin |
| 2 | | | 72 | |
| 3 | BSA- | 0.5 | 24 | Infusion site |
| 3 | Preinfused | | 48 | preinfused with |
| 3 | | | 72 | 1% BSA |

The invention claimed is:

1. A method for treating brain cancer, comprising administering a gene therapy vector and albumin to a subject in need thereof, wherein the gene therapy vector is a viral vector, the albumin and gene therapy vector are administered by infusion into the brain, and the gene therapy vector is administered subsequent to the administration of albumin.

2. The method of claim 1, wherein the cancer is glioma.

3. The method of claim 1, wherein the viral vector is a herpes simplex virus vector.

4. The method of claim 1, wherein the albumin is in isotonic solution.

5. The method of claim 1, wherein the albumin is in artificial CSF.

6. The method of claim 1, wherein the albumin and/or gene therapy vector are administered by infusion via a fine catheter.

7. The method of claim 6, wherein the albumin and/or gene therapy vector are administered by convection enhanced delivery.

8. A method for improving the transduction of gene therapy vectors comprising administering albumin to a subject, wherein the albumin and gene therapy vector are administered by infusion into the brain, and the gene therapy vector is administered subsequent to the administration of albumin.

9. The method of claim 8, wherein the albumin is in isotonic solution.

10. The method of claim 8, wherein the albumin is in artificial CSF.

11. The method of claim 8, wherein the albumin and/or gene therapy vector are administered by infusion via a fine catheter.

12. The method of claim 11, wherein the albumin and/or gene therapy vector are administered by convection enhanced delivery.

* * * * *